(12) United States Patent
Jeglorz et al.

(10) Patent No.: US 9,618,322 B2
(45) Date of Patent: Apr. 11, 2017

(54) PROCESS FOR OPTICAL COHERENCE TOMOGRAPHY AND APPARATUS FOR OPTICAL COHERENCE TOMOGRAPHY

(75) Inventors: Tobias Jeglorz, Nuremberg (DE); Ole Massow, Bergen (DE); Henning Wisweh, Hannover (DE)

(73) Assignee: WAVELIGHT GMBH (DE)

(*) Notice: Subject to any disclaimer, the term of this patent is extended or adjusted under 35 U.S.C. 154(b) by 263 days.

(21) Appl. No.: 14/368,765

(22) PCT Filed: Dec. 28, 2011

(86) PCT No.: PCT/EP2011/006594
§ 371 (c)(1),
(2), (4) Date: Oct. 21, 2014

(87) PCT Pub. No.: WO2013/097877
PCT Pub. Date: Jul. 4, 2013

(65) Prior Publication Data
US 2015/0042949 A1    Feb. 12, 2015

(51) Int. Cl.
| | |
|---|---|
| *A61B 3/10* | (2006.01) |
| *G01B 9/02* | (2006.01) |
| *A61B 5/00* | (2006.01) |
| *G06K 9/62* | (2006.01) |
| *G06K 9/00* | (2006.01) |
| *G01B 11/02* | (2006.01) |

(52) U.S. Cl.
CPC .......... *G01B 9/02041* (2013.01); *A61B 3/102* (2013.01); *A61B 5/0066* (2013.01); *G01B 9/02091* (2013.01); *G01B 11/02* (2013.01); *G06K 9/00214* (2013.01); *G06K 9/6201* (2013.01)

(58) Field of Classification Search
CPC ....................................................... A61B 3/102
USPC ......................................... 351/205, 206, 246
See application file for complete search history.

(56) References Cited

U.S. PATENT DOCUMENTS

| | | | |
|---|---|---|---|
| 7,744,221 B2* | 6/2010 | Wei ........................ | A61B 3/102 351/200 |
| 2007/0115481 A1 | 5/2007 | Toth et al. | |

(Continued)

FOREIGN PATENT DOCUMENTS

| | | |
|---|---|---|
| JP | 2011-087672 | 5/2011 |
| JP | 2011-224264 | 11/2011 |

(Continued)

*Primary Examiner* — Huy K Mai

(57) ABSTRACT

In a process for optical coherence tomography a plurality of first OCT slice images, in each first slice image representing a different slice of an object, are recorded. Subsequently a reference figure that is representative of the three-dimensional contour of at least one structural feature of the object in a given three-dimensional coordinate system is ascertained by feature recognition of the at least one structural feature in the first slice images. Then a plurality of second OCT slice images, each second slice image representing a different slice of the object, are recorded. At least a fraction of the second slice images are displaced in the coordinate system until each second slice image is in feature overlap with the reference figure. Lastly, a set of three-dimensional OCT image data is generated at least from the feature-overlapped second slice images.

22 Claims, 11 Drawing Sheets

(56) References Cited

U.S. PATENT DOCUMENTS

Figure 1:
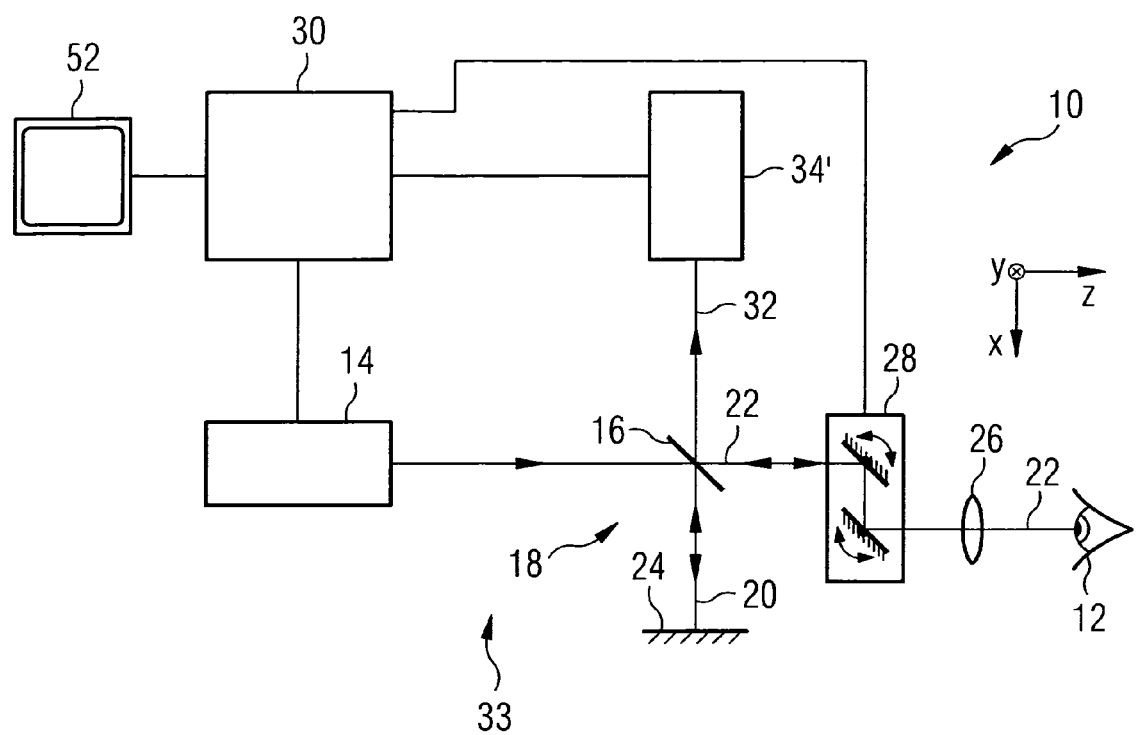

| | | | |
|---|---|---|---|
| 2008/0055543 A1* | 3/2008 | Meyer | A61B 3/102 351/205 |
| 2008/0100612 A1 | 5/2008 | Dastmalchi et al. | |
| 2009/0028403 A1 | 1/2009 | Bar-Aviv et al. | |
| 2011/0134394 A1 | 6/2011 | Srinivasan et al. | |

FOREIGN PATENT DOCUMENTS

| | | |
|---|---|---|
| WO | 2009131655 A2 | 10/2009 |
| WO | 2010117386 A1 | 10/2010 |

\* cited by examiner

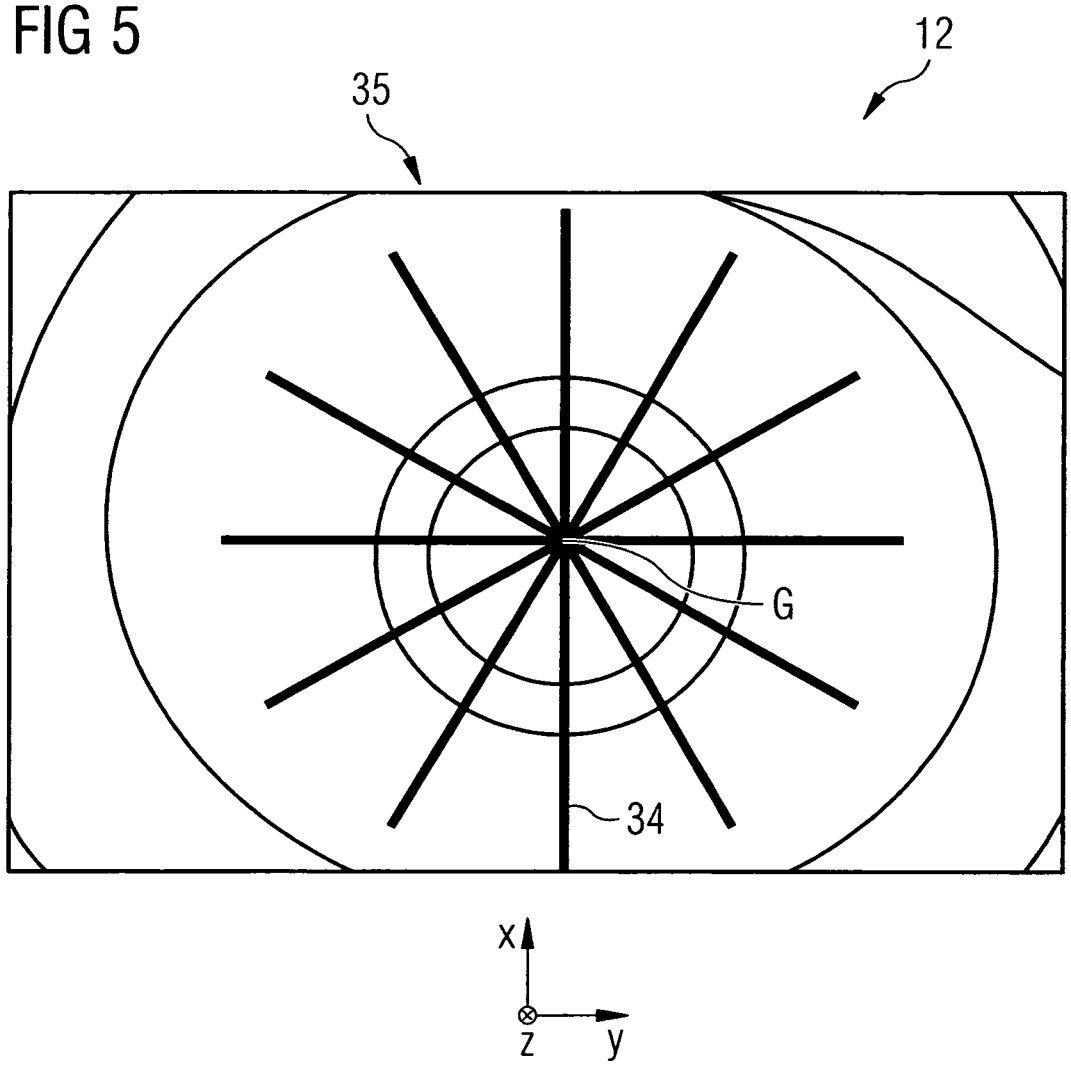

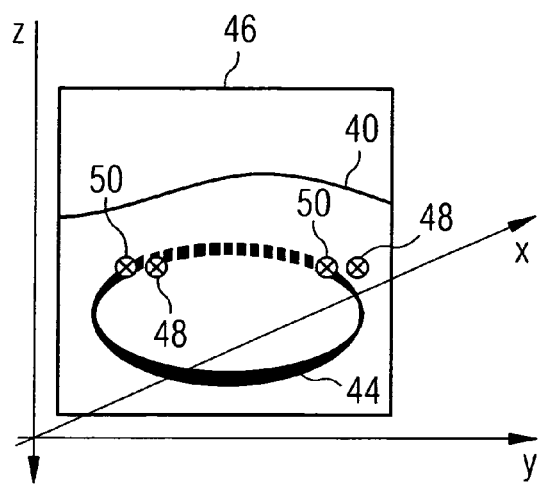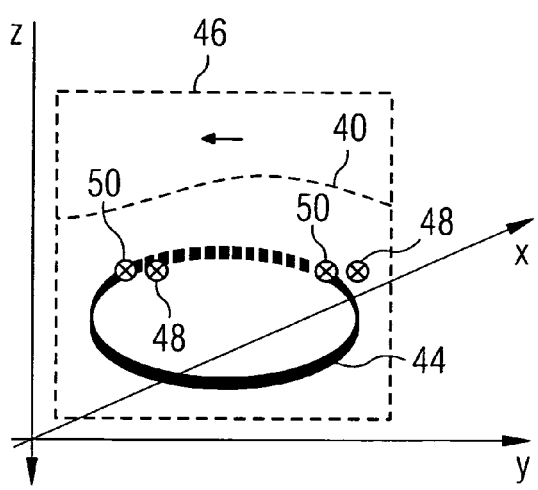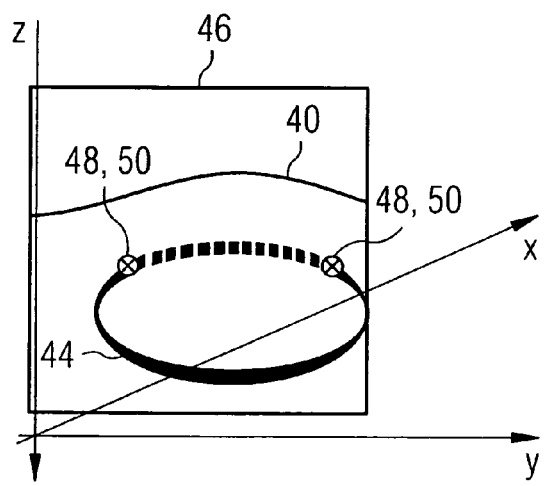

PROCESS FOR OPTICAL COHERENCE TOMOGRAPHY AND APPARATUS FOR OPTICAL COHERENCE TOMOGRAPHY

CROSS REFERENCE TO RELATED APPLICATIONS

This application is a section 371 national stage phase of International Application No. PCT/EP2011/006594, filed 28 Dec. 2011, titled "PROCESS FOR OPTICAL COHERENCE TOMOGRAPHY AND APPARATUS FOR OPTICAL COHERENCE TOMOGRAPHY," which is hereby incorporated by reference in its entirety.

The present invention relates to a process for optical coherence tomography, in particular for generating sets of three-dimensional image data pertaining to an object to be examined. The invention further relates to an apparatus for optical coherence tomography.

For the purpose of creating a three-dimensional (3D for short) tomogram of an object to be examined with the aid of optical coherence tomography (OCT for short), it is conventional to record a large number of OCT slice images oriented in layers with respect to one another within a volume of the object to be scanned and to orient said slice images subsequently with respect to one another. A 3D registration of such a type can be generated by arranging the individual slice images with respect to one another in each instance in the way in which they were arranged originally at the time of the recording thereof in a coordinate system of the recording apparatus.

A problem of this approach, however, is that the eye move during the recording of the slice images representing the 3D tomogram. In the course of the subsequent 3D registration of the individual slice images, imaging errors in the 3D tomogram may occur by reason of motion artefacts.

It is an object of embodiments of the invention to specify a process that enables a three-dimensional representation of an object that can be examined by means of optical coherence tomography. Furthermore, an object of embodiments of the invention is to specify an apparatus that operates in accordance with a process of such a type.

One process provides for recording a plurality of first OCT slice images, each first slice image representing a different slice of an object to be examined. Subsequently a reference figure that is representative of the three-dimensional contour of at least one structural feature of the object is ascertained in a given three-dimensional coordinate system by feature recognition of the at least one structural feature in the first slice images. Then a plurality of second OCT slice images, each second slice image representing a different slice of the object, are recorded. At least a fraction of the second slice images are displaced in the coordinate system until each second slice image is in feature overlap with the reference figure. Finally, a set of three-dimensional OCT image data is generated at least from the feature-overlapped second slice images.

In other words: a plurality of first slice images are recorded, the first slice images representing various longitudinal or cross-sectional projections of at least one structural feature of the object. Then the structural feature is recognised, for example by image processing of each one of the first slice images. From this, interpolation coordinates can be ascertained that represent the position of the structural feature in a coordinate system. A reference figure representing the shape of the structural feature can be adapted to the interpolation coordinates. Subsequent thereto, a plurality of second slice images are recorded which also represent various longitudinal or cross-sectional projections of the structural feature. In each of the second slice images the structural feature is recognised, and corresponding positions of the structural feature in the coordinate system are ascertained. In addition, puncture points can be ascertained that represent the position of points of intersection of each one of the second slice images with the reference figure. The positions of the structural feature can be compared with the puncture points. If for a second slice image not all the positions of the structural feature are congruent with the puncture points, the second slice image is displaced, tilted and/or rotated by coordinate transformation in the coordinate system until such time as the second slice image is oriented with respect to the reference figure in exactly fitting manner and the positions of the structural feature are congruent with the puncture points. For the purpose of creating a 3D tomogram of the object, finally the first and/or second slice images can be assembled to form an overall set of image data.

The present invention consequently makes it possible that during a first (e.g. comparatively short) period of time first slice images are recorded to begin with which may serve to determine the position, orientation and/or size of a reference figure of predetermined shape. The reference figure may subsequently be utilised as a 3D registration support, in order to suitably orient with respect to one another the second slice images recorded during a second period of time (e.g. longer in comparison with the first period of time). Motion artefacts in the 3D tomogram of the object, caused by movement of the object, are thereby avoided. The 3D registration consequently contributes to the creation of a 3D projection of the object with reduced errors.

The first and/or second slice images constitute, for example, so-called B-scans. These represent flat, two-dimensional (2D for short) OCT projections of the object. A B-scan can be obtained on the basis of a plurality of line scans, so-called A-scans. An A-scan constitutes a measured OCT interferogram and represents a rectilinear, one-dimensional (1D for short) OCT projection over an axial distance of the object. A B-scan may be formed from several A-scans of equal length situated in one plane and running parallel to one another. All the slice images and the set of image data may also be stored in a suitable storage medium.

The object to be examined may be, for example, an eye. The object may be any other suitable physical entity that can be imaged, such as a workpiece with internal structural features.

The position and the orientation of the structural feature may reproduce, in substitutional manner, the position and the orientation of the object in a coordinate system. For this purpose the structural feature extends, for example, over an extensive region on or in the object. If the object is an eye, the structural feature may be, for example, the outer and/or inner margin of the iris and/or the limbus of the eye. Alternatively the structural feature may be a surface or internal structural face of the human lens and/or the cornea.

The reference figure may simulate the geometry of the structural feature schematically. For this purpose the reference figure may represent a simplified model of the structural feature that substantially reproduces the position and the orientation of the structural feature in a coordinate system. Accordingly it is conceivable that the reference figure represents a geometrical shape such as an ellipse, a circular disc, a circular disc with concentrically inscribed circular hole, a sphere, a spherical shell, a cylinder, a hollow cylinder with finite thickness of the circumferential surface, or the like. If the structural feature is, for example, the margin of the iris, the reference figure may exhibit a circular shape and/or elliptical shape. If the structural feature is, for example, both the inner and outer margins of the iris, the reference figure may represent a geometrical shape that comprises two circular shapes and/or elliptical shapes that have a certain spatial positioning and orientation with respect to one another.

The term "displacing" refers to changing the position and/or the orientation of an entity in any suitable manner. For example, a coordinate transformation may be applied to the position and/or the orientation to change the position and the orientation, respectively. A coordinate transformation may include at least one spatial translation parallel or antiparallel to the x-, y- and/or z-axes of a coordinate system and/or at least one spatial rotation about an axis of rotation along the x-, y- and/or z-axes and/or a spatial rotation about an axis of rotation between the x-, y- and/or z-axes by a positive or negative angle in the coordinate system. Accordingly, the term "displacing" may include an arbitrary tilting in space. A coordinate transformation preserves some or all the relative spacings between individual constituents of the projection within the second slice image. Merely the position and the orientation of the slice image as such are changed. The space coordinates of each image pixel of the second slice image are affected, but not the colour value or tonal value of the image pixel.

In certain embodiments, a first period of time expended overall for the recording of the plurality of first slice images may be shorter than a second period of time expended overall for the recording of the plurality of second slice images. The first period of time is determined, inter alia, from the number of first slice images, from the number of interferograms recorded per slice image, and from the recording-time of an individual one of these interferograms. The recording-time of an individual interferogram is determined, inter alia, from the exposure-time, from a following period of reworking (for instance, for the sampling of the interferogram, for possible image-processing steps such as Fourier transformations, image-recognition processes and such like) and from the time needed for storage. Analogous remarks apply to the second period of time.

In certain embodiments, the number of first slice images may be smaller than the number of second slice images. For example, the ratio of the number of first slice images to the number of second slice images amounts to 1:2, 1:5, 1:10 or 1:100.

Furthermore, the recording time for a first slice image may be shorter than the recording time for a second slice image. For example, the exposure time, the period of reworking and/or the storage time of the first slice images is/are shorter than corresponding time intervals for the second slice images. In particular, for each slice image a plurality of A-scans of the object are recorded that is smaller than the number of A-scans for the second slice images. Accordingly, a first slice image may consist of 200 A-scans, and the frequency of recording A-scans may amount to 70 kHz. A second slice image consists, for example, of 500 to 2000 A-scans, which are recorded at a recording-rate from 20 kHz to 70 kHz.

In certain embodiments, the recording-time for a first slice image may be sufficiently short that motion artefacts during the recording of the first slice image, caused by typical movements of the object, are substantially avoided.

The first slice images may be recorded by means of B-scans that are distributed over the object in a regular pattern. For example, the first slice images can be recorded by means of B-scans that are distributed in a cross-grid pattern. For example, first slice images oriented orthogonally with respect to one another are acquired, whereby in each instance two adjacent first slice images exhibit a constant spacing from one another.

As an alternative, the first slice images may be oriented with respect to one another in the shape of a star in such a manner that the first slice images intersect one another in a straight line. The straight line may coincide with an axis of symmetry of the object and/or may run through points of the object that have been marked out. For example, the straight line is centred with the pupillary centre of an eye and runs along the optical axis thereof or through the apex of the cornea.

The first slice images may be recorded in such a distribution pattern that points of intersection of the first slice images with the reference figure are situated, distributed substantially at equal spacings, along the reference figure after the reference figure has been adapted to the first slice images.

Additionally or alternatively, the first slice images may be recorded in such a distribution pattern that the number n of points of intersection at which the reference figure intersects the surface normals of the first slice images at an angle within the range of more than 30° and less than 60°, after the reference figure has been adapted to the first slice images, amounts to at least $2(N-2)$, where N is the number of first slice images. In other words: of the N first slice images of, for example, an orthogonal cross pattern, after the reference figure has been adapted at least $N-2$ first slice images are intersected by the reference figure in such a manner that the reference figure includes with the respective surface normals of the first slice images at the respective point of intersection an angle of more than 30° and less than 60°. In this case there are a total of at least $n=2(N-2)$ such points of intersection, whereby the n points of intersection differ from one another, i.e. amongst themselves are not situated on top of one another.

Additionally or alternatively, the first slice images may be recorded in such a distribution pattern that the number n of points of intersection at which the reference figure intersects the first slice images, after the reference figure has been adapted to the first slice images, suffices for describing the geometry of the reference figure.

The second slice images may also be recorded by means of B-scans that are distributed over the object in a certain pattern. The pattern may include, for example, a cross-grid pattern. In this case the second slice images may have been oriented orthogonally and/or parallel to one another. Additionally or alternatively, the pattern may include two cross-grid patterns placed over one another in angle-offset manner. For example, the angle amounts to about 45°. Additionally or alternatively, the pattern may include three cross-grid patterns placed over one another in angle-offset manner. For example, the angle amounts to about 60°.

The pattern of the second slice images may be irregular. For instance, the grid-line density of a cross pattern in a central region of the reference figure is lower than in a region of the reference figure remote from the centre. For this purpose a spacing of two adjacent second slice images oriented parallel to one another that intersect the region of the reference figure remote from the centre may be smaller than a spacing of two adjacent second slice images oriented parallel to one another that intersect the central region of the reference figure. If the second slice images also contain cross-sectional projections of the cornea of a human eye, on the basis of the irregular pattern the aspherical regions of the cornea can be represented with higher resolution than can regions of the cornea in the vicinity of the apex of the cornea. The density of cross-sectional projections of the cornea is accordingly higher in a region representing the aspherical region of the cornea. Positions of these cross-sectional projections may serve as interpolation nodes for the segmentation of structural layers in the object being examined, or for an adaptation of a predetermined surface shape to the cornea by means of Zernike polynomials.

The process may additionally include the following step: by image processing in a first and/or second slice image an indication of motion artefacts that have occurred during the recording of the respective slice image is recognised. An indication of motion artefacts includes, for example, a discontinuity, a waviness, a contraction and/or an elongation within a profile in the slice image representing the structural feature and/or a low signal-to-noise ratio (SNR for short) of adjacent A-scans of a slice image. This step may take place 'online' before the next slice image is acquired in accordance with the distribution pattern. If motion artefacts are discernible within a first and/or second slice image, the acquisition of the defective slice image may be repeated until the slice image is present in flawless manner. But the acquisition of an individual first and/or second slice image may take place so quickly that the recording time required for the acquisition is short in comparison with a timescale that is typical of eye movements.

An apparatus for optical coherence tomography comprises an OCT image-acquisition unit and a computer arrangement that has been set up to control the OCT image-acquisition unit in such a manner that the latter records a plurality of first OCT slice images, each first slice image representing a different slice of an object, to ascertain a reference figure that is representative of the three-dimensional contour of at least one structural feature of the object in a given three-dimensional coordinate system by feature recognition of the at least one structural feature in the first slice images, to control the OCT image-acquisition unit in such a manner that the OCT image-acquisition unit records a plurality of second OCT slice images, each second slice image representing a different slice of the object, to displace at least a fraction of the second slice images in the coordinate system until each second slice image is in feature overlap with the reference figure, and to generate a set of three-dimensional OCT image data at least from the feature-overlapped second slice images.

The apparatus may have been set up to bring about a process, described above, for optical coherence tomography.

To the extent that a process or individual steps of a process for optical coherence tomography is/are described in this description, the process or individual steps of the process can be executed by an appropriately configured apparatus. Analogous remarks apply to the elucidation of the mode of operation of an apparatus that executes process steps. To this extent, apparatus features and process features of this description are equivalent.

Figure 2:
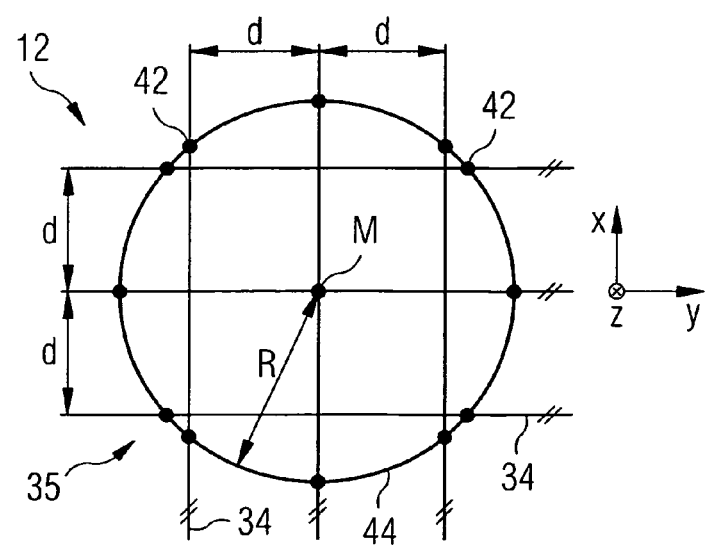
Figure 3:
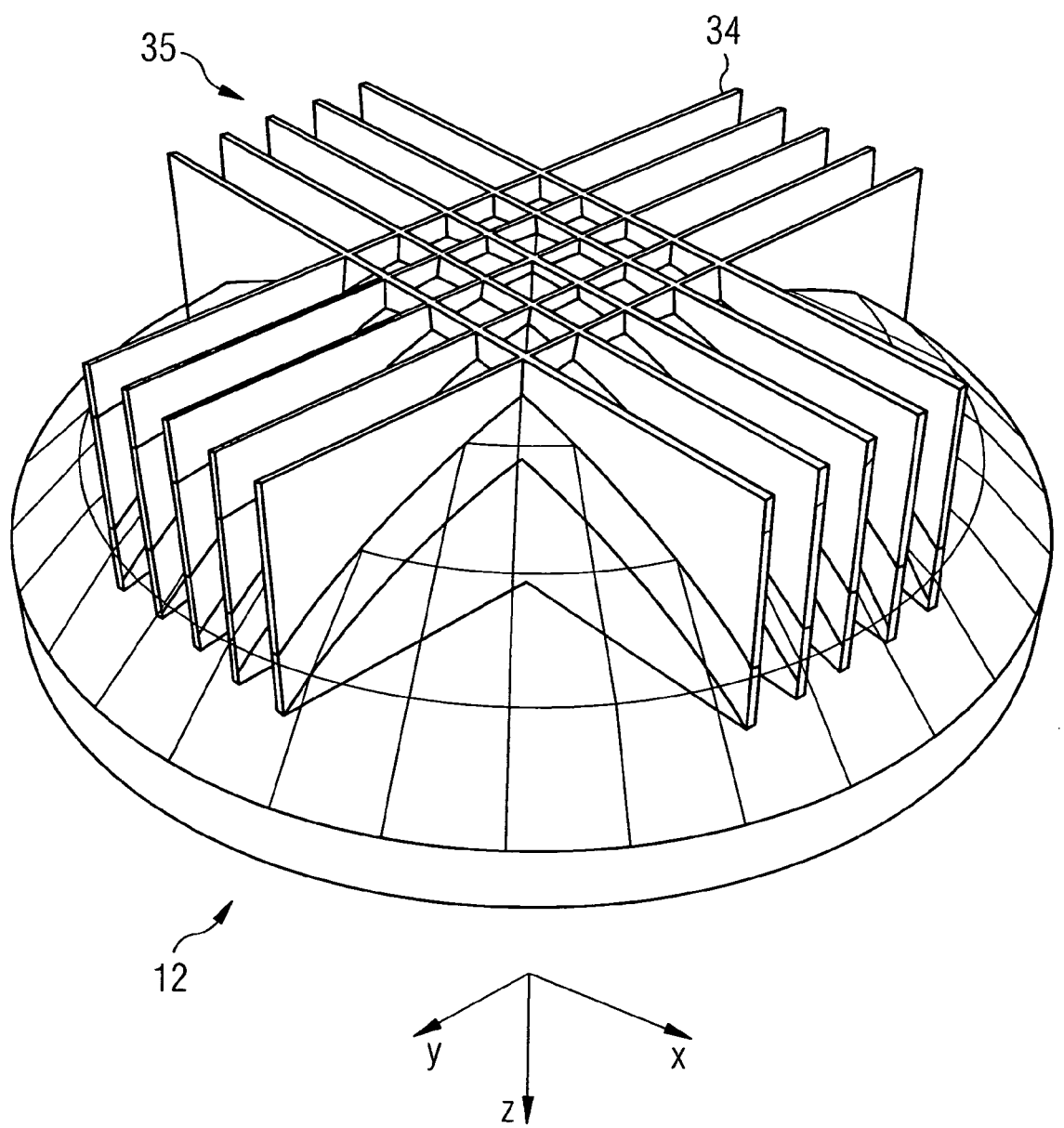
Figure 4A:
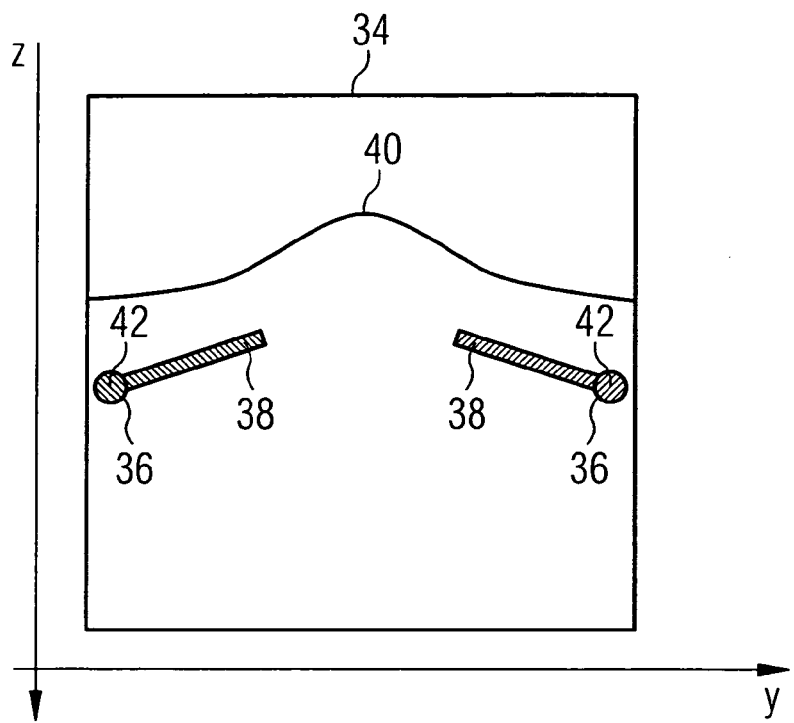
Figure 4B:
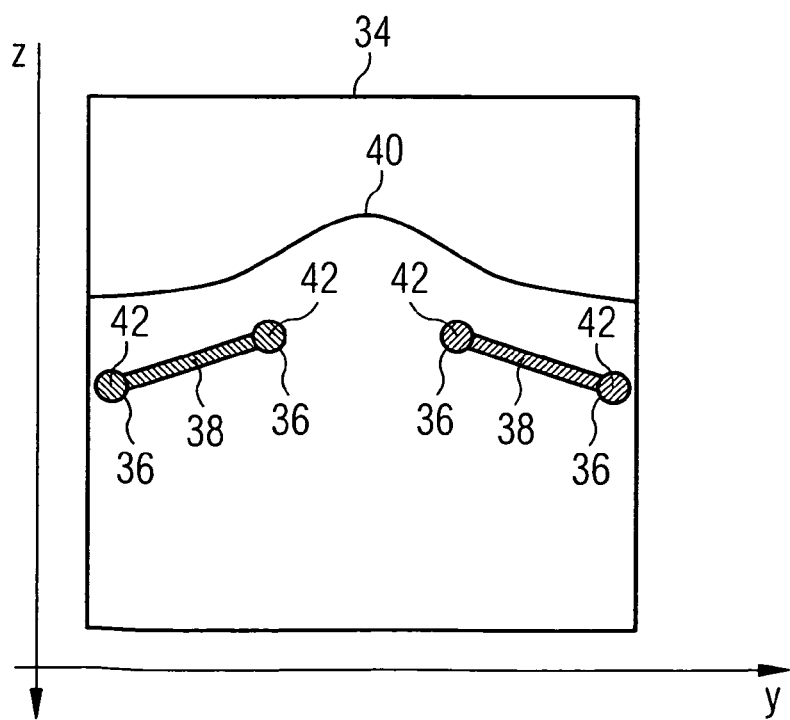
Figure 6A:
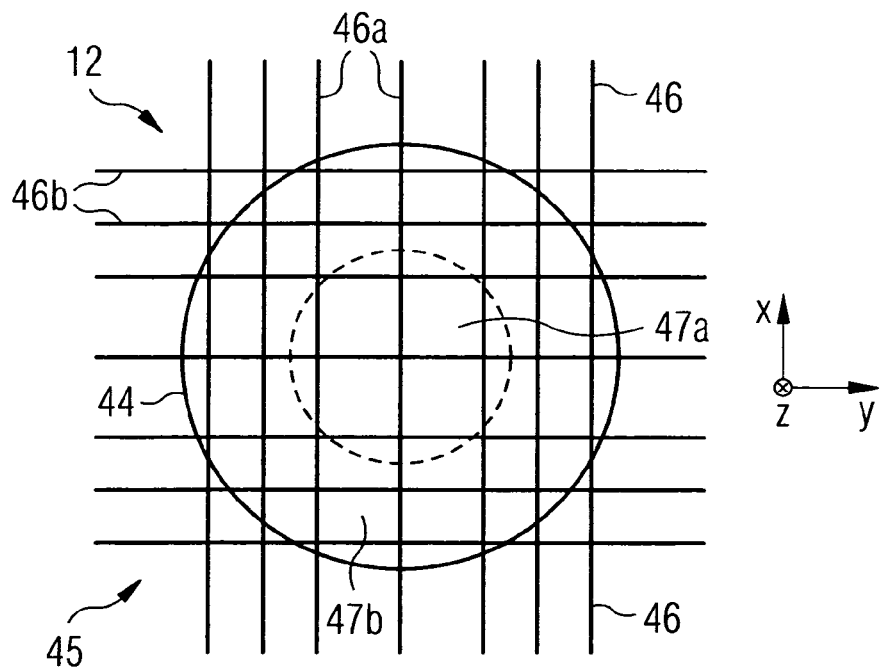
Figure 6B:
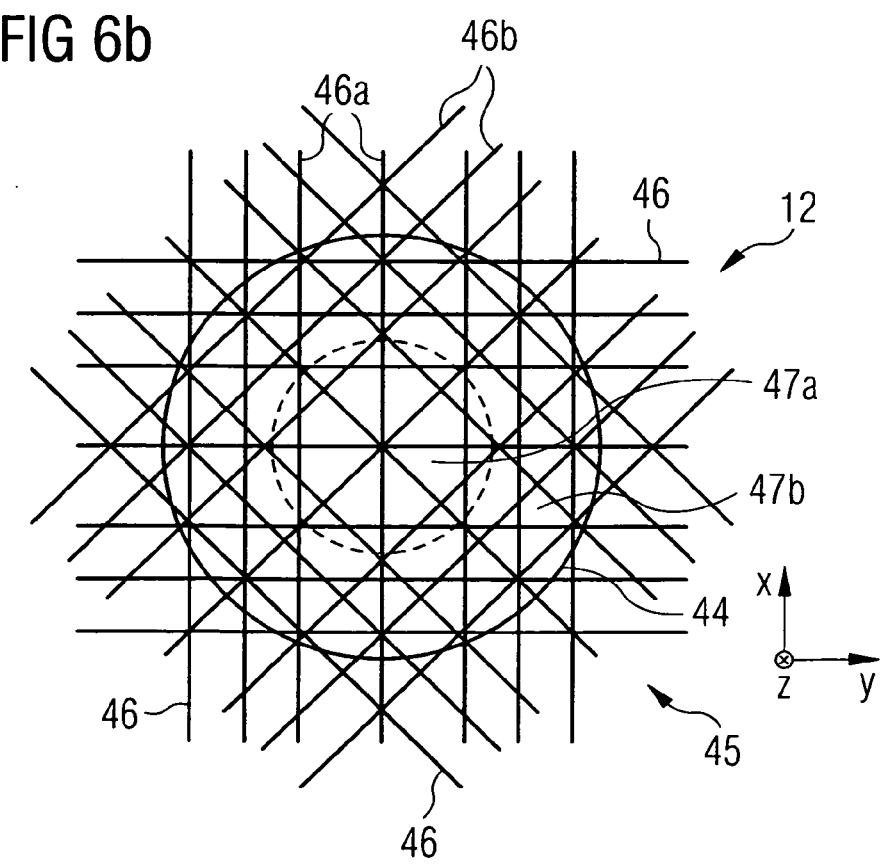
Figure 7A:
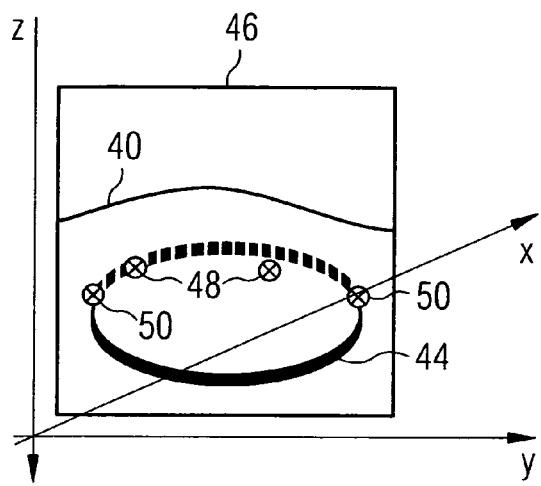
Figure 7B:
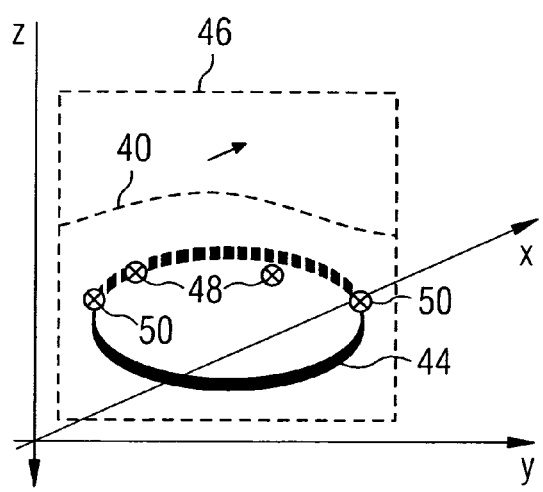
Figure 7C:
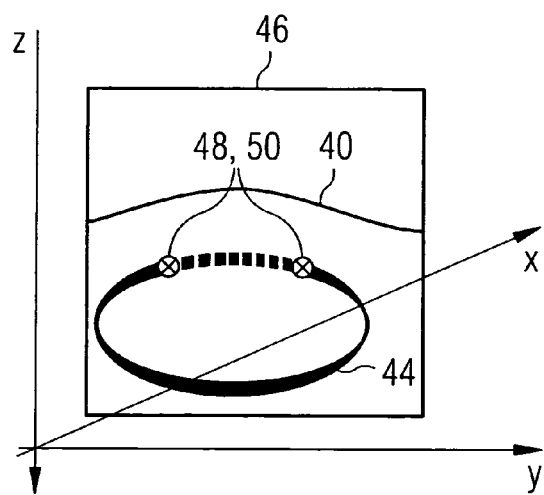
Figure 9A:
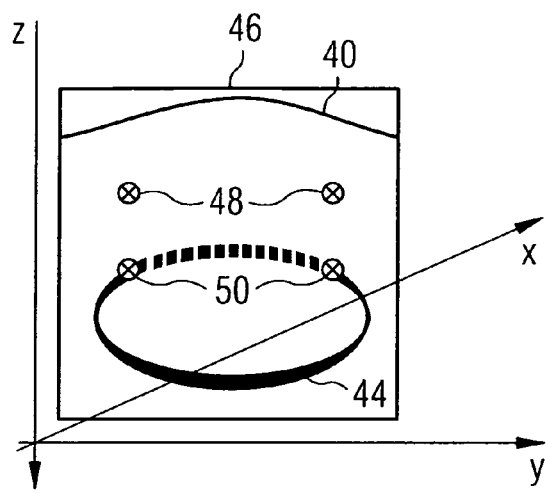
Figure 9B:
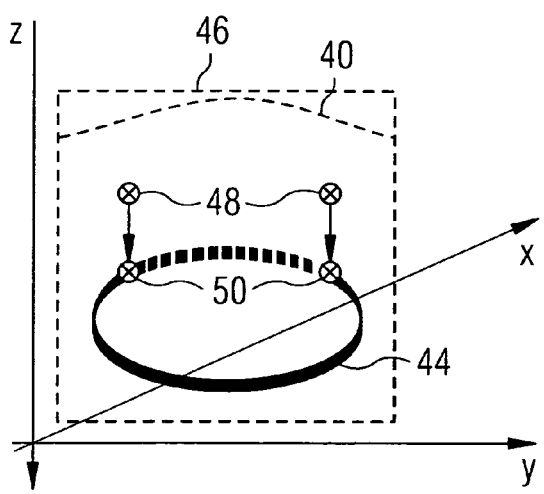
Figure 9C:
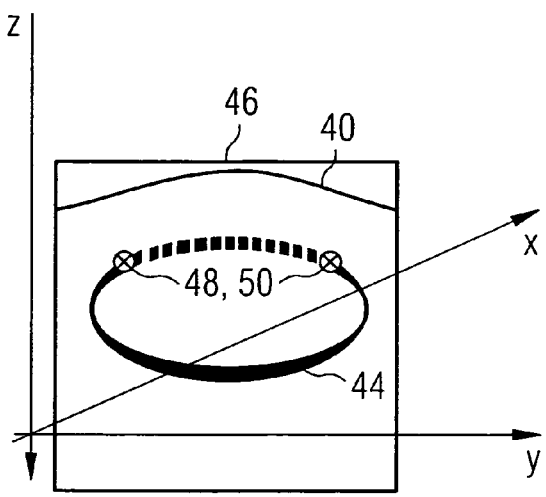
Figure 10A:
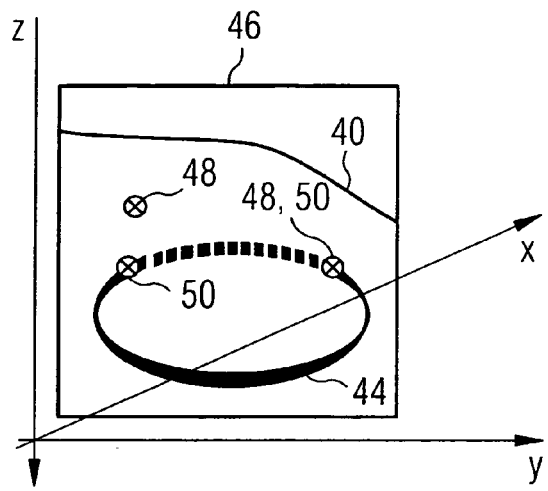
Figure 10B:
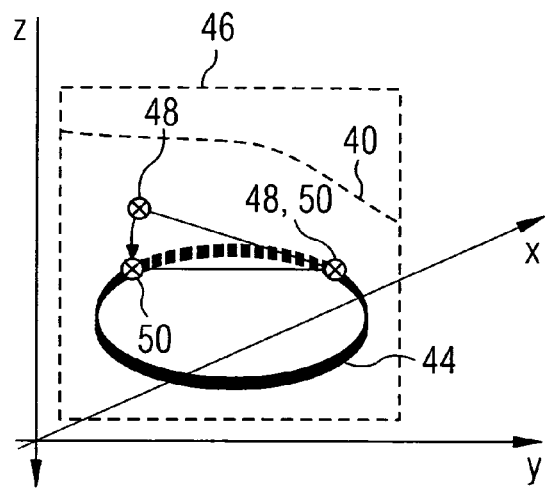
Figure 10C:
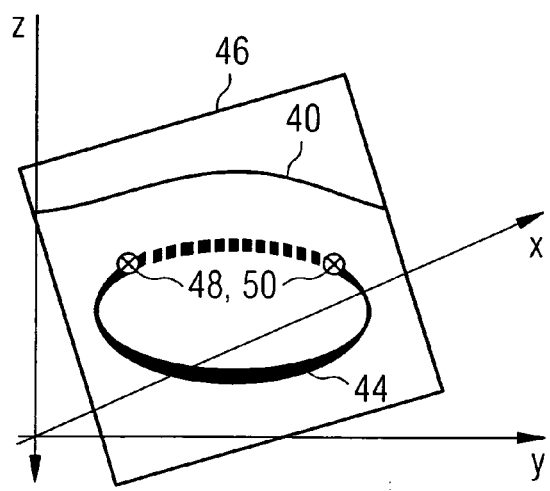

The invention will be elucidated further in the following on the basis of the appended drawings, of which:

FIG. 1 shows, in schematic block representation, elements of an apparatus for optical coherence tomography according to one embodiment, FIG. 2 shows, in top view schematically, an example of a distribution pattern in which the first slice images are recorded, with a reference figure drawn in, FIG. 3 shows, in a three-dimensional view schematically, the distribution pattern from FIG. 2, FIGS. 4a and 4b show schematically examples of a first slice image, FIG. 5 shows, in top view schematically, a further example of a distribution pattern in which the first slice images are recorded, FIGS. 6a and 6b show, in top view schematically, examples of distribution patterns in which the second slice images are recorded, FIGS. 7a to 7c show schematically an example relating to the displacing of a second slice image parallel to an x-axis until the second slice image is in feature overlap with a reference figure, FIGS. 8a to 8c show schematically an example relating to the displacing of a second slice image antiparallel to a y-axis until the second slice image is in feature overlap with a reference figure, FIGS. 9a to 9c show schematically an example relating to the displacing of a second slice image parallel to a z-axis until the second slice image is in feature overlap with a reference figure, FIGS. 10a to 10c show schematically an example relating to the rotation of a second slice image about an axis of rotation running parallel to an x-axis until the second slice image is in feature overlap with a reference figure, and FIGS. 11a to 11e show schematically an example relating to the displacing of a second slice image until the second slice image is in feature overlap with a reference figure.

The apparatus for optical coherence tomography in FIG. 1—denoted generally therein by 10—serves for creating 3D tomograms of an object shown in the exemplary case as a human eye 12. The optical coherence tomography is based, for example, on so-called time-domain (TD for short) OCT or on so-called frequency-domain (FD for short) OCT.

The apparatus 10 includes a light-source 14 for emitting coherent light. The light-source 14 is designed, for example, for the purpose of FD OCT as a tuneable light-source or emits a spectrum of coherent light that is broadband within the frequency space. The light emitted from the light-source 14 is directed onto a beam-splitter 16. The beam-splitter 16 is a constituent part of a Michelson interferometer 18 and splits up the incident optical output in accordance with a predetermined splitting ratio, for example 50:50. One ray 20 runs within a reference arm; the other ray 22 runs within a specimen arm. Instead of the free-space setup represented in FIG. 1 the Michelson interferometer 18 may also have been realised partly or entirely with the aid of fibre-optic components.

The light that has been branched off in the reference arm impinges onto a mirror 24 which reflects the light back onto the beam-splitter 16 collinearly. For the purpose of TD OCT the mirror 24 may be displaceable along the direction of propagation of the ray 20. The light that has been branched off in the specimen arm impinges onto the object 12 to be examined, which back-scatters or reflects back the light in the direction of the beam-splitter 16.

In FIG. 1 a three-dimensional Cartesian coordinate system of the apparatus 10 has been drawn in schematically which serves as coordinate system in the following. In this connection the z-axis represents the direction of propagation of the light ray 22 in the region immediately upstream of the object 12.

Within the specimen arm further optical elements 26 and components 28 are provided, which have been set up to focus the light ray 22 coming in from the beam-splitter 16 onto the object 12 and to adjust the focus position (for example in the lateral directions x, y or in all three directions in space x, y, z). A computer arrangement 30 controls the components 28 for the purpose of obtaining 1D, 2D and/or 3D tomograms.

The light back-scattered from the object 12 in the specimen arm is collinearly superimposed at the beam-splitter 16 with the light reflected back from the mirror 24 in the reference arm so as to form an interference beam 32. The optical path lengths in the reference arm and specimen arm are substantially equally long, so that the interference beam 32 displays an interference between the constituent rays 20, 22 from reference arm and specimen arm. A detector 34' registers the intensity of the interference beam 32 as a function of the time, the wavelength and/or the wave number. For this purpose the detector 34' may take the form of a photodiode or spectrometer.

The signal registered by the detector 34' is transferred to the control arrangement 30 which ascertains 2D OCT slice images therefrom. In this sense the computer arrangement 30, the light-source 14, the detector 34' and the Michelson interferometer 18, inclusive of the optical elements 26 and the components 28, may be understood as an OCT image-acquisition unit 33 which is controlled by the computer arrangement 30.

For the purpose of creating a 3D tomogram of the object 12 the computer arrangement 30 controls the components 28 in accordance with such a scan pattern that a 3D registration of the acquired slice images within a scanned volume of the object 12 with respect to one another can be undertaken. This process will be described in detailed manner in the following with reference to FIGS. 2 to 11.

First of all, a plurality of first slice images 34, each first slice image representing a different slice of the object 12, are recorded and are stored in a memory of the computer arrangement 30. The first slice images 34 represent OCT B-scans which are obtained from a large number of OCT A-scans. A first slice image 34 consists of, for example, 200 A-scans. Furthermore, a short exposure-time is chosen in which the individual A-scans are recorded. The rate of recording of A-scans amounts to, for example, 70 kHz.

As shown in FIG. 2, in the present exemplary case three horizontal and three vertical first slice images 34 are acquired in an orthogonal cross pattern 35 similar to a chessboard. In this example the horizontal and vertical first slice images 34 are arranged parallel to one another, the spacing d of adjacent first slice images 34 being constant for all adjacent slice images 34. In FIG. 3 the distribution pattern, shown in FIG. 2, of the slice images 34 and a part of the eye 12 are illustrated again three-dimensionally.

As an alternative to the distribution pattern shown in FIGS. 2 and 3, the distribution pattern, shown in FIG. 5, of first slice images 34 is also possible. In this case the first slice images 34 have been oriented with respect to one another in the shape of a star in such a manner that the first slice images 34 intersect one another in a straight line G. In the example shown in FIG. 5 the straight line G is centred with the pupillary centre of the eye 12 and runs along the optical axis of the eye 12, that is to say, substantially parallel to the z-axis.

A first slice image 34 is shown in FIGS. 4a and 4b. The first slice images 34 represent cross-sectional projections of at least one structural feature 36 of the object 12. In FIG. 4a the structural feature 36 is, for example, the outer margin of the iris 38 in the eye 12. In FIG. 4b the structural feature 36 is, for example, the outer and inner margins of the iris 38. Besides the iris 38, in the first slice image 34 the cornea 40, for example, is also imaged.

In the first slice images 34 which have been prepared the computer arrangement 30 now recognises the structural feature 36 on the basis of an image-recognition algorithm and determines the position(s) 42 thereof in the coordinate system of the apparatus 10. In FIGS. 2, 4a and 4b these positions 42 are labelled by means of small circles filled in with black.

As shown in FIG. 2, the computer arrangement 30 subsequently adapts a reference FIG. 44 that is representative of the three-dimensional contour of the structural feature 36 to the positions 42 ascertained beforehand serving as interpolation nodes. In FIG. 2 the reference FIG. 44 represents a circular shape in imitation of the margin of the iris 38, which is predetermined by a midpoint M (i.e. a 3D space coordinate) and a further parameter R defining the radius. The adapting or fitting of the reference FIG. 44 to the interpolation nodes 42 is based on a mathematical optimisation method in order to determine (to estimate) the unknown parameters M and R of the reference FIG. 44 for a series of interpolation nodes 42.

The spacing d of the slice images 34 is chosen in such a way that the interpolation nodes 42 have an almost equidistant spacing on the periphery of the reference FIG. 44 after the reference FIG. 44 has been adapted to the first slice images 34.

Additionally or alternatively, the first slice images 34 can be recorded in such a distribution pattern 35 that the number n of points of intersection at which the reference FIG. 44 intersects the first slice images 34, in each instance at an angle within the range of more than 30° and less than 60° in relation to the surface normal of the respective slice image 34, amounts to at least 2(N−2), where N is the number of first slice images 34, after the reference FIG. 44 has been adapted to the first slice images 34. This is represented in exemplary manner in FIG. 2: of the six first images 34 (i.e. N=6) of the orthogonal cross pattern 35, after the reference FIG. 44 has been adapted four first slice images 34 are intersected by the reference FIG. 44 in such a manner that the reference FIG. 44 includes with the respective surface normals of the first slice images 34 at the respective point of intersection an angle of more than 30° and less than 60° (i.e. n=2(N−2)=2(6−2)=8).

Additionally or alternatively, the first slice images 34 can be recorded in such a distribution pattern 35 that the number n of points of intersection at which the reference FIG. 44 intersects the first slice images 34 suffices for describing the geometry of the reference FIG. 44 after the reference FIG. 44 has been adapted to the first slice images 34. This is again represented in FIG. 2: the six first slice images 34 of the orthogonal cross pattern 35 are intersected by the reference FIG. 44 at twelve points of intersection after the reference FIG. 44 has been adapted. Each of these twelve points of intersection is described in three-dimensional space by three parameters (space coordinates x, y, z), so that a total of 36 parameters are available for fitting the reference FIG. 44. For example, the circle shown in FIG. 2 is described by a midpoint in three-dimensional space (consisting of three parameters) and a radius (vector) in three-dimensional space (likewise consisting of three parameters). For the purpose of fitting the reference FIG. 44, at least six parameters are accordingly required, so that the 36 parameters of the twelve points of intersection between the reference FIG. 44 and the first slice images 34 are sufficient.

Subsequently a plurality of second slice images 46, each second slice image representing a different slice of the object 12, are recorded and stored. The second slice images 46 also represent OCT B-scans which are obtained from a large number of OCT A-scans. The second slice images 46 consist, for example, of 2000 A-scans per B-scan, the A-scans being recorded at a recording-rate from, for example, 20 kHz to 70 kHz. In comparison with the first slice images 34, the second slice images 46 therefore offer higher statistics and image quality. This permits higher-quality, in the sense of a signal-to-noise ratio, second slice images 46 to be created.

As shown in FIGS. 6a and 6b, the second slice images 46, in the course of the acquisition thereof, are distributed over the object 12 in accordance with an irregular pattern 45. In FIGS. 6a and 6b, in addition the reference FIG. 44 ascertained beforehand has been drawn in. The irregular distribution pattern includes a cross-grid pattern, the grid-line density of which in a central region 47a of the reference FIG. 44 is lower than in a region 47b of the reference FIG. 44 remote from the centre. In FIGS. 6a and 6b the central region 47a and the region 47b remote from the centre are separated from one another in exemplary manner by a dashed line. Consequently a spacing of two adjacent second slice images 46a oriented parallel to one another in the central region 47a of the reference FIG. 44 is larger than a spacing of two adjacent second slice images 46b oriented parallel to one another in the region 47b of the reference FIG. 44 remote from the centre.

In FIG. 6a the second slice images 46 are arranged in such a manner that they are oriented orthogonally and/or parallel to one another. But alternatively the distribution pattern shown in FIG. 6b is also possible, in which the second slice images are arranged in such a manner that they are oriented orthogonally and/or parallel to one another and/or intersect one another at an angle of 45 degrees. Accordingly, the irregular pattern includes two cross-grid patterns placed on top of one another in angle-offset manner.

In FIGS. 7a to 11e schematic representations of second slice images 46 are shown. The second slice images 46 likewise represent cross-sectional projections of the structural feature 36. In the second slice images 46 the cornea 40, for example, is also imaged. As in the case of the first slice images 34, on the basis of image processing the computer arrangement 30 ascertains in the second slice images 46 the structural feature 36 and determines the position(s) 48 thereof in the coordinate system of the apparatus 10. In FIGS. 7a to 11e these positions 48 are labelled by means of small black circles with inscribed black cross.

The reference FIG. 44 can also be seen in FIGS. 7a to 11e, wherein the margin thereof is represented by a continuous line if the reference FIG. 44, viewed from the observer, runs spatially in front of the second slice image 46, and the margin thereof is represented by a dashed line if the reference FIG. 44, viewed from the observer, runs spatially behind the second slice image 46.

For each second slice image 46 the computer arrangement 30 ascertains by calculation the positions of puncture points 50 at which the reference FIG. 44 intersects the second slice image 46. The (original) position and orientation of a second slice image 46 which are required for this purpose are predetermined by the distribution pattern 45. The puncture points 50 are labelled in FIGS. 7a to 11e, like the positions 48, by means of small black circles with inscribed black cross. The puncture points 50 are situated at the transition from the continuous margin to the dashed margin of the reference FIG. 44.

If not all the positions 48 are in congruence with the puncture points 50, the computer arrangement 30 displaces a second slice image 46 in the coordinate system of the apparatus 10 until all the positions 48 in the second slice image 46 are congruent with the puncture points 50. For this purpose the computer arrangement 30 ascertains a suitable coordinate transformation for the second slice image 46. In the course of the transformation all the relative spacings between individual projection constituents 40, 48 within the second slice image 46 are preserved. Merely the position and the orientation of the slice image 46 as such are changed.

In FIGS. 7a to 11e exemplary displacements, rotations or coordinate transformations are shown, on the basis of which second slice images 46 are oriented with respect to a reference FIG. 44. Small arrows shown therein illustrate the respective displacement or rotation.

Accordingly, FIGS. 7a to 7c show a translation of a second slice image 46 parallel to the x-axis. In FIG. 7a the computer arrangement 30 recognises that the positions 48 are not congruent with the puncture points 50, since the spacing between the two positions 48 is shorter than between the puncture points 50. The reason for this is that the eye 12 has been displaced effectively antiparallel to the x-axis during the period of time between creation of the reference FIG. 44 and the recording of the second slice image 46. With a view to compensating the eye movement, the computer arrangement 30 carries out a coordinate transformation for the second slice image 46, whereby the space coordinates of each image pixel in the second slice image 46 are corrected in such a manner that after the coordinate transformation the positions 48 are congruent with the puncture points 50.

In this way the second slice images 46 are oriented, image by image, with respect to the reference FIG. 44 and are stored. This type of 3D registration enables the creation of 3D tomograms of the object 12 that are free from motion artefacts. In this manner, motion artefacts such as, for example, level errors, rotation errors orthogonal to the optical axis and/or lateral movements can be compensated. Accordingly, the computer arrangement 30 generates from the feature-overlapping second slice images 46 a set of three-dimensional OCT image data which is then displayed on a display unit 52 of the apparatus 10 as a 3D tomogram of the object 12 to be examined.

In FIGS. 8a to 8c a further coordinate transformation of a second slice image 46 is shown, in the course of which the second slice image 46 is displaced antiparallel to the y-axis. In FIGS. 9a to 9c a coordinate transformation for a second slice image 46 is again shown. In this case the displacement is effected parallel to the z-axis of the coordinate system of the apparatus 10.

In FIGS. 10a to 10c a spatial rotation of a second slice image 46 is shown. Although in FIG. 10a one position 48 is initially congruent with one puncture point 50, the second position 48 does not tally with the second puncture point 50. The second slice image 46 is therefore rotated about an axis of rotation running parallel to the x-axis, see FIG. 10b.

In FIGS. 11a to 11e a somewhat more complex transformation of a second slice image 46 is shown. In this example the reference FIG. 44 represents both the inner and outer margins of the iris 38 of the eye 12. The reference figure consists of two circular shapes arranged parallel to one another, the midpoints of which lie on a straight line perpendicular to the surfaces of the circular shapes.

Figure 11A:
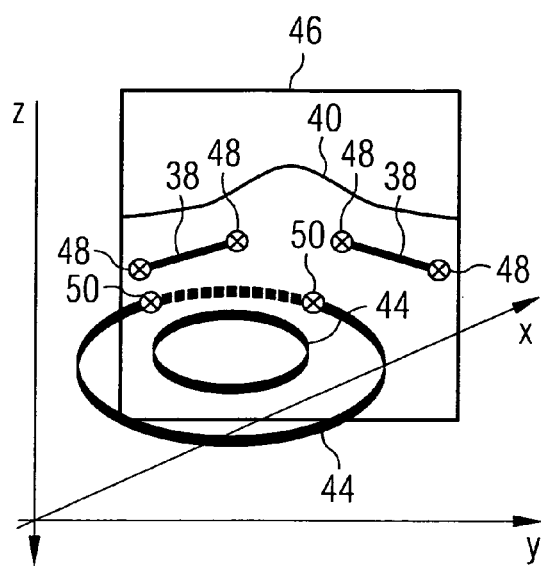
Figure 11B:
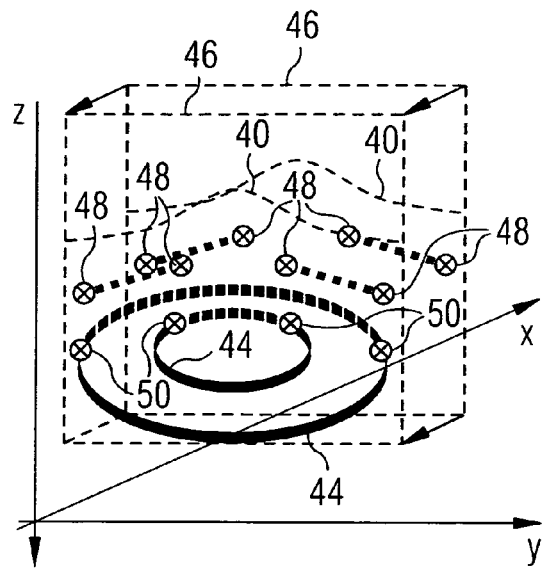
Figure 11C:
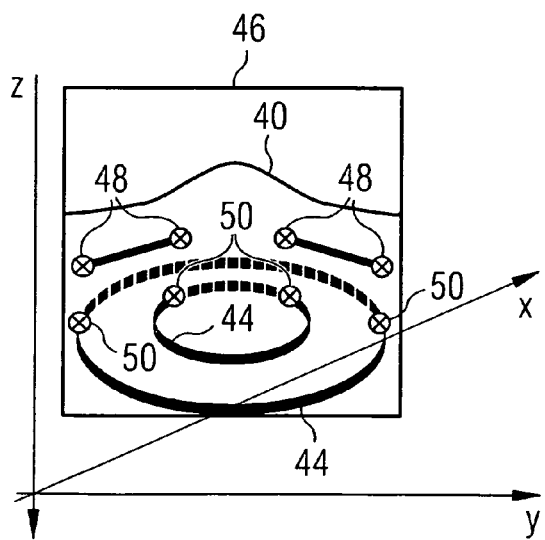
Figure 11D:
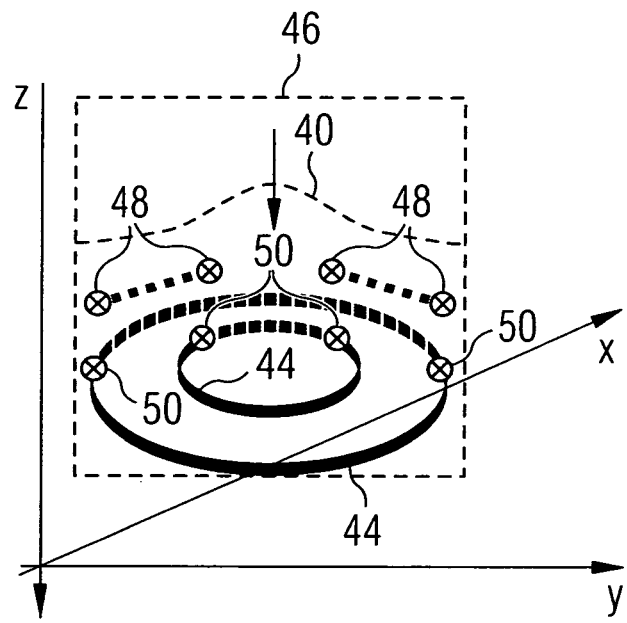
Figure 11E:
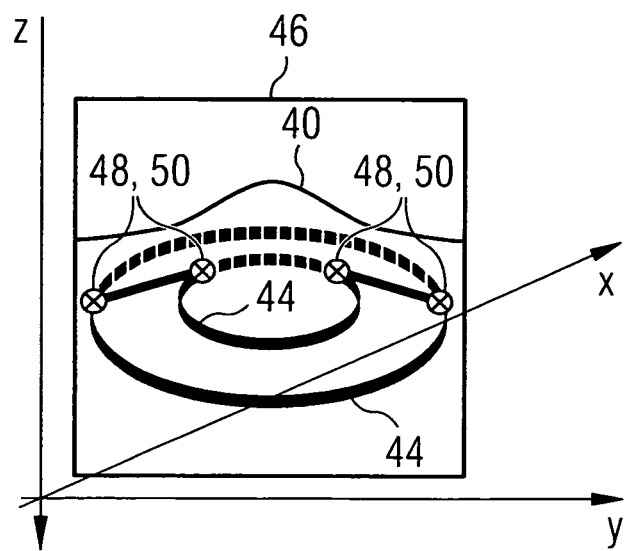

In FIG. 11a it can be discerned that in the second slice image 46 four positions 48 corresponding to a cross-section through the inner and outer margins of the iris were recognised by the computer arrangement 30 but the reference FIG. 44 intersects the second slice image 46 merely at two puncture points 50. In FIG. 11b it can be seen how the second slice image 46 is therefore displaced firstly antiparallel to the x-axis until four puncture points 50 with relative spacings corresponding to the relative spacings of the positions 48 are present, see FIG. 11c. In FIG. 11d a spatial translation of the second slice image 46 parallel to the z-axis is subsequently effected until, as shown in FIG. 11e, a total overlap of features occurs.

The computer arrangement 30 has furthermore been set up to recognise, by image processing in a first and/or second slice image 34, 46, an indication of motion artefacts that have arisen during the recording of the respective slice image 34, 46. If motion artefacts are recognisable within a slice image 34, 46, the computer arrangement 30 controls the OCT image-acquisition unit 33 in such a manner that the acquisition of the defective slice image 34, 46 is repeated. But the acquisition of a slice image 34, 46 is effected so quickly that the individual B-scan is free from motion artefacts.

Unless expressly stated otherwise, identical reference symbols in the Figures stand for identical or identically-acting elements. In other respects, an arbitrary combination of the features elucidated in the Figures in connection with individual embodiments is conceivable.

The invention claimed is:

1. Process for optical coherence tomography, comprising:
recording a plurality of first OCT slice images, each first slice image representing a different slice of an object;
ascertaining a reference figure that is representative of the three-dimensional contour of at least one structural feature of the object in a given three-dimensional coordinate system by feature recognition of the at least one structural feature in the first slice images;
recording a plurality of second OCT slice images, each second slice image representing a different slice of the object, a time period for recording a second slice image is longer than a time period for recording a first slice image;
displacing at least a fraction of the slice images in the coordinate system until each second slice image is in feature overlap with the reference figure; and
generating a set of three-dimensional OCT image data at least from the feature-overlapped second slice images.

2. Process according to claim 1, wherein the number of first slice images is smaller than the number of second slice images.

3. Process according to claim 1, wherein for each slice image a plurality of A-scans of the object are recorded, the number of A-scans for the first slice images being in each instance smaller than for the second slice images.

4. Process according to claim 1, wherein the first slice images are recorded by means of B-scans that are distributed over the object in a regular pattern.

5. Process according to claim 1, wherein the first slice images are recorded by means of B-scans that are distributed in a cross-grid pattern.

6. Process according to claim 1, wherein the first slice images are recorded in such a distribution pattern that points of intersection of the first slice images with the reference figure are situated, distributed substantially at equal spacings, along the reference figure and/or that the number n of points of intersection at which the reference figure intersects the first slice images in each instance at an angle within the range of more than 30° and less than 60° in relation to the surface normals of the respective slice image amounts to at least 2(N−2), where N is the number of first slice images, and/or that the number n of points of intersection at which the reference figure intersects the first slice images suffices for describing the geometry of the reference figure after the reference figure has been adapted to the first slice images.

7. Process according to claim 1, wherein the second slice images are recorded by means of B-scans that are distributed over the object in an irregular pattern.

8. Process according to claim 7, wherein the irregular pattern includes a cross-grid pattern, the grid-line density of which in a central region of the reference figure is lower than in a region of the reference figure remote from the centre.

9. Process according to claim 7, wherein the irregular pattern includes at least two cross-grid patterns placed over one another in angle-offset manner, whereby in particular the pattern includes two cross-grid patterns placed over one another in angle-offset manner with an angle of about 45° or includes three cross-grid patterns placed over one another in angle-offset manner with an angle of about 60°.

10. Process according to claim 1, wherein the ascertaining of the reference figure includes an adapting of at least one circular figure to feature positions of the at least one structural feature in the first slice images.

11. Process according to claim 1, wherein the object is a human eye and the at least one structural feature includes an inner iris margin and/or an outer iris margin of the eye and/or a limbus of the eye.

12. Apparatus for optical coherence tomography, comprising an OCT image-acquisition unit and a computer arrangement that has been set up to:
control the OCT image-acquisition unit in such a manner that the OCT image-acquisition unit records a plurality of first OCT slice images, each first slice image representing a different slices of an object;
ascertain a reference figure that is representative of the three-dimensional contour of at least one structural feature of the object in a given three-dimensional coordinate system by feature recognition of the at least one structural feature in the first slice images;
control the OCT image-acquisition unit in such a manner that the OCT image-acquisition unit records a plurality of second OCT slice images, each second slice image representing a different slice of the object, a time period for recording a second slice image is longer than a time period for recording a first slice image;
displace at least a fraction of the second slice images in the coordinate system until each second slice image is in feature overlap with the reference figure, figure; and
generate a set of three-dimensional OCT image data at least from the feature-overlapped second slice images.

13. Apparatus according to claim 12, wherein the OCT image-acquisition unit has been set up to record a number of first slice images and a number of second slice images, the number of first slice images being smaller than the number of second slice images.

14. Apparatus according to claim 12, wherein the OCT image-acquisition unit has been set up to record for each slice image a plurality of A-scans of the object, the number of A-scans for the first slice images being in each instance smaller than for the second slice images.

15. Apparatus according to claim 12, wherein the OCT image-acquisition unit has been set up to record the first slice images by means of B-scans that are distributed over the object in a regular pattern.

16. Apparatus according to claim 12, wherein the OCT image-acquisition unit has been set up to record the first slice images by means of B-scans that are distributed in a cross-grid pattern.

17. Apparatus according to claim 12, wherein the OCT image-acquisition unit has been set up to record the first slice images in such a distribution pattern that points of intersection of the first slice images with the reference figure are situated, distributed substantially at equal spacings, along the reference figure and/or that the number n of points of intersection at which the reference figure intersects the first slice images in each instance at an angle within the range of more than 30° and less than 60° in relation to the surface normal of the respective slice image amounts to at least 2(N−2), where N is the number of first slice images, and/or that the number n of points of intersection at which the reference figure intersects the first slice images suffices for describing the geometry of the reference figure after the reference figure has been adapted to the first slice images.

18. Apparatus according to claim 12, wherein the OCT image-acquisition unit has been set up to record the second slice images by means of B-scans that are distributed over the object in an irregular pattern.

19. Apparatus according to claim 18, wherein the OCT image-acquisition unit has been set up to record the second slice images in accordance with the irregular pattern, the irregular pattern including a cross-grid pattern, the grid-line density of which in a central region of the reference figure is lower than in a region of the reference figure remote from the centre.

20. Apparatus according to claim 18, wherein the OCT image-acquisition unit has been set up to record the second slice images in accordance with the irregular pattern, the irregular pattern including at least two cross-grid patterns placed over one another in angle-offset manner, whereby in particular the pattern includes two cross-grid patterns placed over one another in angle-offset manner with an angle of about 45° or includes three cross-grid patterns placed over one another in angle-offset manner with an angle of about 60°.

21. Apparatus according to claim 12, wherein the computer arrangement has been set up to ascertain the reference figure by an adapting of at least one circular figure to feature positions of the at least one structural feature in the first slice images.

22. Apparatus according to claim 12, wherein the object is a human eye and the at least one structural feature includes an inner iris margin and/or an outer iris margin of the eye and/or a limbus of the eye.

* * * * *